(12) United States Patent
Cohen

(10) Patent No.: US 7,131,208 B2
(45) Date of Patent: *Nov. 7, 2006

(54) METHOD, DEVICE AND CARTRIDGE FOR MEASURING FLUCTUATIONS IN THE CROSS-SECTIONAL AREA OF HAIR IN A PRE-DETERMINED SCALP AREA

(75) Inventor: Bernie Cohen, Miami, FL (US)

(73) Assignee: Bernard Cohen Technology, LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/105,241

(22) Filed: Apr. 13, 2005

(65) Prior Publication Data
US 2005/0229418 A1    Oct. 20, 2005

Related U.S. Application Data

(63) Continuation-in-part of application No. 10/826,943, filed on Apr. 16, 2004, now Pat. No. 6,993,851.

(51) Int. Cl.
*A61B 5/107* (2006.01)
*G01B 21/02* (2006.01)

(52) U.S. Cl. .......................................... 33/512; 33/784
(58) Field of Classification Search .................. 33/512, 33/511, 783, 784, 813, 818, 819, 828, 831
See application file for complete search history.

(56) References Cited

U.S. PATENT DOCUMENTS

| | | | | |
|---|---|---|---|---|
| 1,962,357 A | * | 6/1934 | Nessler | 33/512 |
| 1,962,518 A | * | 6/1934 | Nessler | 33/512 |
| 1,981,911 A | * | 11/1934 | Engelsman | 33/512 |
| 4,170,827 A | * | 10/1979 | Katz et al. | 33/712 |
| 4,217,695 A | * | 8/1980 | Chapman et al. | 33/736 |
| 4,520,565 A | * | 6/1985 | Maggiore | 30/201 |

(Continued)

FOREIGN PATENT DOCUMENTS

JP    2003126065 A    *    5/2003

OTHER PUBLICATIONS

Elise A. Olsen, *Current and Novel Method for Assessing Efficacy of Hair Growth Promoters in Pattern Hair Loss*, Feb. 2003, pp. 253-262.

*Primary Examiner*—R. Alexander Smith
(74) *Attorney, Agent, or Firm*—Thomas R. Vigil; Welsh & Katz, Ltd.

(57) ABSTRACT

A flexible measuring tape is extended from a predetermined location on a face a predetermined distance to a location on a scalp. A 2 cm by 2 cm square bundle of hair about that location is isolated. The bundle of isolated hair is captured in a slit in a two-part cartridge, one part being slidable in the other part about a changeable length slit 1 mm wide. The cartridge is placed in an "L" shaped end of a plunger extending from a first end of a body of a measuring device. The plunger is drawn into the body of the device to compress the hair in the changeable length slit as the two parts of the cartridge are pushed together between an end of the "L" and the first end of the body. A spring is provided on the plunger between a second end of the body of the device and an inner end of a knob at an outer end of the plunger. The spring applies the same load regardless of the bundle's size and urges the "L" shaped end toward the body to compress the bundle of hair and the amount of compressed hair is read off of a gauge as DDI, Density-Diameter Index, which represents the cross-sectional area of the compressed bundle of hair. After the measurement is made, the smaller part is pulled part way out of the larger part of the cartridge so the cartridge easily can be pulled off of the bundle of hair and discarded.

30 Claims, 16 Drawing Sheets

U.S. PATENT DOCUMENTS

| | | | |
|---|---|---|---|
| 4,573,267 A * | 3/1986 | Grohoski et al. | 30/133 |
| 4,665,741 A | 5/1987 | Kabacoff et al. | 73/149 |
| 5,170,669 A * | 12/1992 | Kawano | 73/847 |
| 5,327,656 A * | 7/1994 | Nissimov | 33/512 |
| 5,495,677 A * | 3/1996 | Tachikake et al. | 33/784 |
| 6,993,851 B1 * | 2/2006 | Cohen | 33/512 |

* cited by examiner

METHOD, DEVICE AND CARTRIDGE FOR MEASURING FLUCTUATIONS IN THE CROSS-SECTIONAL AREA OF HAIR IN A PRE-DETERMINED SCALP AREA

CROSS REFERENCE TO RELATED APPLICATIONS

This application is a continuation in part of U.S. application Ser. No. 10/826,943, filed Apr. 16, 2004 now U.S. Pat. No. 6,993,851.

BACKGROUND OF THE INVENTION

1. Field of the Invention

The present invention relates to a method, device and a two piece cartridge for measuring fluctuations in the cross sectional area of a bundle of hair for the purpose of documenting the clinical course of medical hair loss disorders and the effectiveness of hair growth treatments and/or for the purpose of indirectly calculating the severity of balding disorders or efficacy of hair growth treatment as evidenced by a decrease or increase in hair population and/or hair shaft diameter.

2. Description of the Related Art

Heretofore, a hair volume-measuring device used for measure of hair damage was disclosed in the Kabacoff et al. U.S. Pat. No. 4,665,741.

Also, see the hair measurement methods disclosed in "Current and Novel Methods for Assessing Efficacy of Hair Growth Promoters in Pattern Hair Loss" in J. Am. Acad. Dermatol, 2003; 48:253–62.

Hair shedding is a condition characterized by loss of hairs of normal-sized diameters. It is one of the two major categories of hair loss. Shedding is diffusely distributed over the scalp and may be the sign of several medical abnormalities and toxicities. It may physiologically follow high fever, cessation of birth control pills, or childbirth. Shedding is characterized by the appearance of skin on the scalp where hair was once present. Shedding may be quantified by measuring the density of hairs present in an area of one-centimeter square of scalp. Hair density usually is measured by closely cutting the scalp hair (about 2 mm long in an area 5 mm×5 mm) and then counting the remaining cut hairs present on the scalp and multiplying that value times 4. The hair density of normal individuals in the absence of shedding ranges between 120 to 200 hairs per sq cm of scalp.

Hair thinning is a condition characterized by the gradual miniaturization of individual scalp hairs. It is the second major category of hair loss, and by far the more common. The appearance of hair loss is the result of decreasing diameters resulting in the eventual absence of hairs. Thinning (like shedding) also is characterized by the appearance of skin on the scalp where hair was once present. Thinning affects an estimated 75% of men and 10% of women. Unlike shedding, it is not diffuse in its distribution over the entire scalp surface, but almost always appears in a pattern, with hair loss on the top of the scalp. Thinning characteristically spares the posterior and sides of the lower scalp, (see Zone 10 as pictured in FIG. 19) creating a familiar horse-shaped fringe that persists in spite of the most advanced cases.

Thinning occurs in healthy individuals and is referred to as balding, pattern balding, male or female pattern alopecia, androgenctic alopecia, male or female pattern balding. It is considered normal in 75% of men. And, although it may occur in healthy women, it may indicate an endocrine abnormality in a small group of women.

Early pattern balding is difficult to recognize and difficult to quantify. Simple density measurements (as performed in shedding) are of little value because there is a mixed population of both normal-sized and miniaturized hairs. When density counts are performed, a normal and miniaturized hair would each be counted as one hair. Therefore, in order to detect and quantify thinning in a meaningful manner, the actual hair mass (the collective cross sections of hair from a pre-determined area of scalp) must be measured. This alone would reflect the density of hairs and the array of mixed diameters that are present.

In order to quantify pattern and diffuse hair loss, scientists have commonly used three basic methods:
1. Hair density count or target-area hair count
2. Clinical photography
3. Hair weight.

Quantification of hair loss by measuring the collective cross sections in a pre-determined area of scalp has not been reported in the scientific literature nor disclosed in prior U.S. Patents.

The three commonly used methods are described in more detail below:

Density count or target-area hair count. The density of closely cropped hair in an area of scalp is compared to a known normal range of values, which are 150 to 250 hairs per sq cm. To determine if a hair growth product is efficacious, before and after treatment evaluations are performed. To determine the percent loss of density of a single individual, the density on the top part of the scalp (the area of loss) may be compared to the density on the lower back and sides (the normal and permanent hair zone). The percent hair loss is calculated by dividing the hair count in the hair loss area by the hair count in the permanent zone.

This method is quite imprecise in conditions of thinning, because it measures only the number of hairs and makes no allowance for their variations in diameter. The method is used in a simple office setting because it is a bit more precise than clinical photography. It requires closely cropping the hair and directly examining the scalp exam with a hand lens or video microscope. The method may be brought to a higher level of precision if macrophotographs of the area are taken and enlarged and then only the hairs above a certain diameter (usually 40 microns) are counted.

Clinical photography: Photography is performed comparing the patient's hair loss area to the permanent zone. It may also compare the patient's hair loss zone to a picture of the same zone of a patient with no hair loss, or of a prior or subsequent state of loss in the same patient. To determine if a hair growth product is efficacious, before and after treatment evaluations are performed. In this manner, the growth or loss is grossly quantified by visual observation alone. No insight is gained into whether or not the hair loss is the result of thinning or shedding. Photography is quite imprecise and obscured by various hairstyles and hair lengths. It is however the most common form of hair loss documentation because it is rapid, requires not special training and is easily archived. It requires the cutting of hair to a uniform length, standard photo equipment lighting, and care positioning of the subject, to yield any kind of comparable data.

Hair weight: A small area of hair (usually 5 mm×5 mm) is shaved from a balding area. The patient returns in 30 days and the newly grown hair is cut and weighed. To determine if a hair growth product is efficacious, before and after treatment evaluations are performed. In cases of pattern loss, the procedure may be performed in the permanent zone (lower posterior and lateral horseshoe shaped zone) and compared to the value in the thinning zone of the same patient. The percent hair loss may be calculated by dividing the hair weight in the thinning area by the hair weight in the permanent zone. Hair weight is a very precise method of measuring hair loss because it considers both the number of hairs and their diameters and the hair length in its calculation. Its disadvantage is that the sample size represents a relatively small sample of the scalp surface, but because it measures hair length as well, it may not be as meaningful as thought.

Furthermore it is a very tedious process, requiring strict humidity controls, and is impractical to perform in a clinical setting. It also requires cutting off hair. It is used primarily by commercial laboratories to measure the effectiveness of hair-growing preparations i.e. finasteride, dutasteride, and minoxidil.

BRIEF SUMMARY OF THE INVENTION

According to the present invention there is provided a method and device for measuring fluctuations in the cross sectional area of a section of hair as it relates to the quantification and clinical course of medical hair loss disorders or the effectiveness or progress of hair loss treatment. The method and device are used for determining the cumulative cross-section of hairs within a pre-measured area. The method and device uses a much larger sample of scalp surface than the hair weight method, hair count method, and hair cutting is not required. The length of the hair is not considered a factor in the evaluation because of wide variations of individual styling would make it impossible, and clinically irrelevant. The method of the present invention is easy to perform in a non-laboratory setting and employs a new hand-held device. The method and device allow physicians and hair care professionals to track and document the status of patients, suffering from scalp hair thinning or shedding, at any time in the course of their evaluation or treatment. The method and device may be used to quantitatively evaluate the effectiveness of hair growing preparations and drugs and quantify the severity and clinical course of other medical hair loss disorders. The method and device may be used to detect early decreases in hair diameter—the predictive hallmark of balding—many years before it is apparent.

In practicing the method of the present invention, a predetermined area of hair-bearing skin or scalp is isolated by any of several means. Typically a 2×2 cm of scalp hair is manually isolated using a comb or combing element and fixed in place using 1×3" gummed papers printed with a centimeter scale which are aligned and overlapped in the configuration of a 2×2 cm square. Alternatively, a 2×2 cm area may be isolated by using any device that demarcates the periphery of the area, such as with a ruler and washable ink, marking pen, marking template and/or using a simple comb-like device that is 2 cm. in length, which simultaneously bundles the hair and demarcates the perimeter of the area.

In one embodiment, the bundle of hair is captured in a slit in a two-part cartridge of the present invention (one part being slidable in the other part about a changeable length slit 1 mm wide) which is then placed in an "L" or "J" shaped end of a plunger extending from a first end of a body of a measuring mechanism or device of the present invention. The plunger is drawn into the body of the device of the present invention to compress the hair in the slit as the two parts of the cartridge are pushed together between an end of the "L" or "J" and the first end of the body. A spring is provided on the plunger between a second end of the body of the device and an inner end of a knob at an outer end of the plunger. The spring urges the "L" or "J" shaped end toward the body to compress the bundle of hair and the amount of compressed hair is read off of a gauge on the body of the device and the L shaped end is sheathed by the cartridge to isolate it from surrounding hair for reasons of hygiene. This measurement is referred to as the DDI or Density-Diameter Index and represents the cumulative density and diameter of all hairs in the bundle.

The normal range of DDI's is 3.00–4.00 mm and less than 3.0 for fine hair. After the measurement is made, the smaller part is pulled part way out of the larger part of the cartridge so the cartridge easily can be pulled off of the bundle of hair and discarded.

In another embodiment, the bundle is snared by a lightweight spring-loaded hook-like ("J" shaped) arm, which is drawn into a body of the device of the present invention. The device comprises a hair-trapping element including a "J" shaped end that extends through a boss and has a hair-receiving slot. The device further includes an anvil on an end surface of the boss positioned adjacent the slot whereby relative movement between the "J" shaped end and the anvil compresses the hair received in the slot. A heavyweight compression spring is provided in the device, which bears against the boss. Alternatively the device can have an anvil that moves into a stationary slot.

The bundle is captured in the slot and automatically immobilized against the anvil on the boss. The slot is 1 mm wide and preferably between 7–12 mm high and relative movement between the anvil and the slot measures the height of the hair. By engaging the heavy compression spring, the load on the column of trapped hair may be precisely maintained and thereby kept constant in repeated measurements. This is important because the hair bundle is quite compressible. The mm height of the hair column is displayed on an LED window of an integrated micrometer head that causes relative movement between the anvil and the slot. If a mechanical height-measuring gauge is incorporated in the design of the device, it is displayed on the face of an analog dial. If an electronic height-measuring gauge is incorporated into the device, the height is displayed on an LED window. The height of hair in the trapping hair-receiving slot is expressed as an arbitrary value that shall be called the density-diameter index, the hair mass, the hair mass index, the cross-sectional index, the cumulative cross-sectional index, or the combined cross-sectional index.

The method is performed in the area of thinning and also in the fringe of permanent hair growth on the back and sides of the scalp. The index value of the thinning area is divided by the index value of the permanent area. The percent loss of hair mass in the thinning area is thus derived. It is believed that the method and device of the present invention may have profound medical significance for the following reason: It is a known medical fact that an individual with thinning must lose half of the hair mass in an area of the scalp, before it is obvious to the casual observer that any hair has been lost. This can also be demonstrated by the casual observers inability to tell the difference between a toupee with 200 hairs per sq cm and a toupee with 100 hairs per sq cm. This observation however translates to the following: By the time an individual realizes that he is "losing hair" he has already lost half of his hair. The device of the present invention enables hair professionals and physicians to measure the hair mass in the pre-balding normal-looking areas of the scalp and compare these values to the hair mass value in the permanent zone. The device therefore detects the earliest changes in hair diameter, the predictive hallmark of balding. In this way one can detect whether or not there is hair loss years before it is visually obvious to the patient or his physician. The patient is alerted to the early hair loss and may enjoy the advantages of starting therapy before the loss has significantly advanced. The method and device may also be used to track and quantify the progressive hair loss of individuals with untreated balding, or track and quantify the therapeutic response of hair to drugs and devices intended to grow hair.

DETAILED DESCRIPTION OF THE INVENTION

Figure 1:
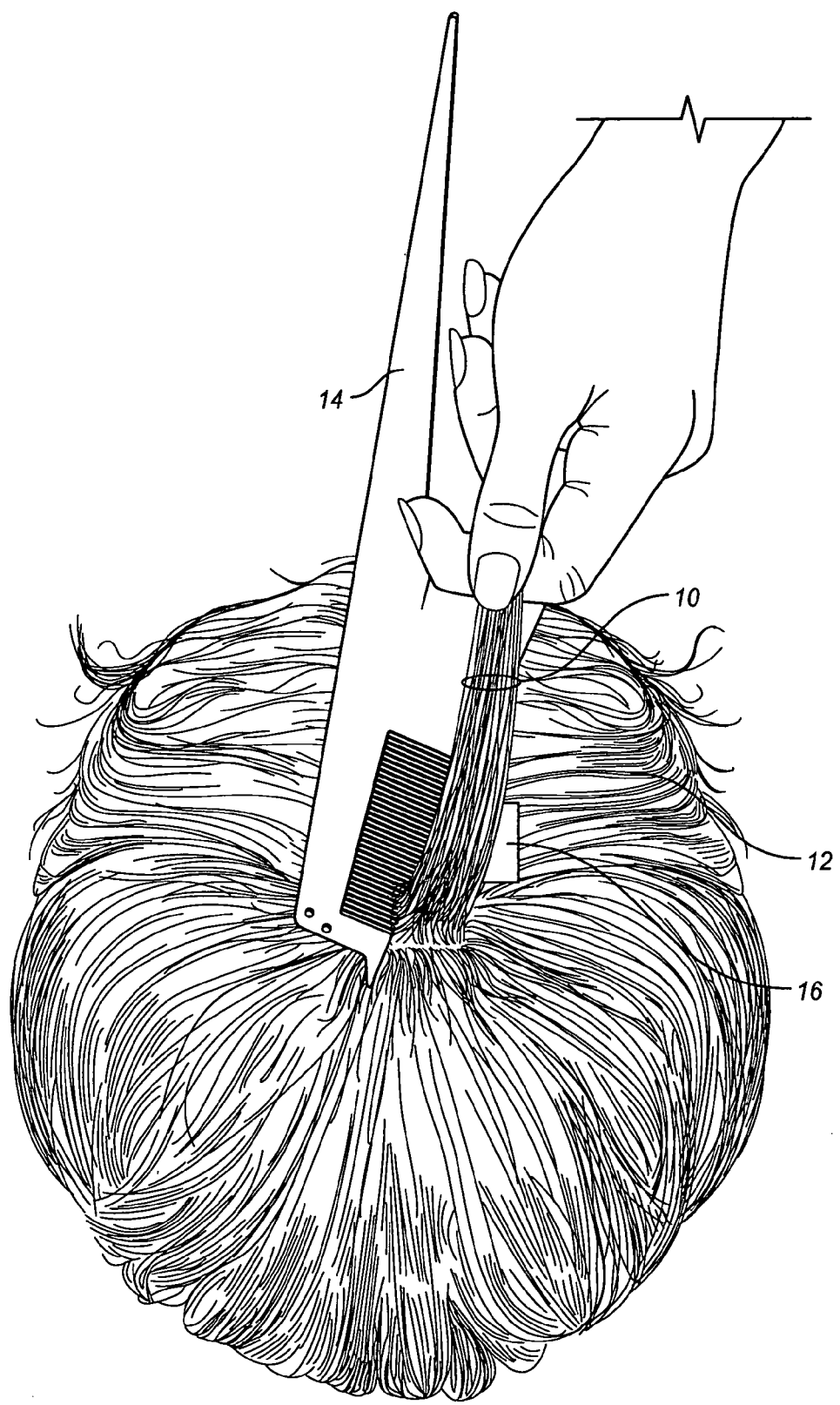
FIG. 1 is a top view of a scalp showing a section or bundle of hair that is combed from a delineated section of scalp with a combing element and shows one side of the section of scalp being delineated by a gummed label.

Referring now to FIG. 1 there is illustrated therein a combed bundle or section of hair 10 from a scalp 12, that has been combed with a comb or combing element 14. The bundle 10 of hair is delineated from a predetermined area of the scalp 12 by a gummed label 16, without cutting the bundle 10 of hair.

Figure 2:
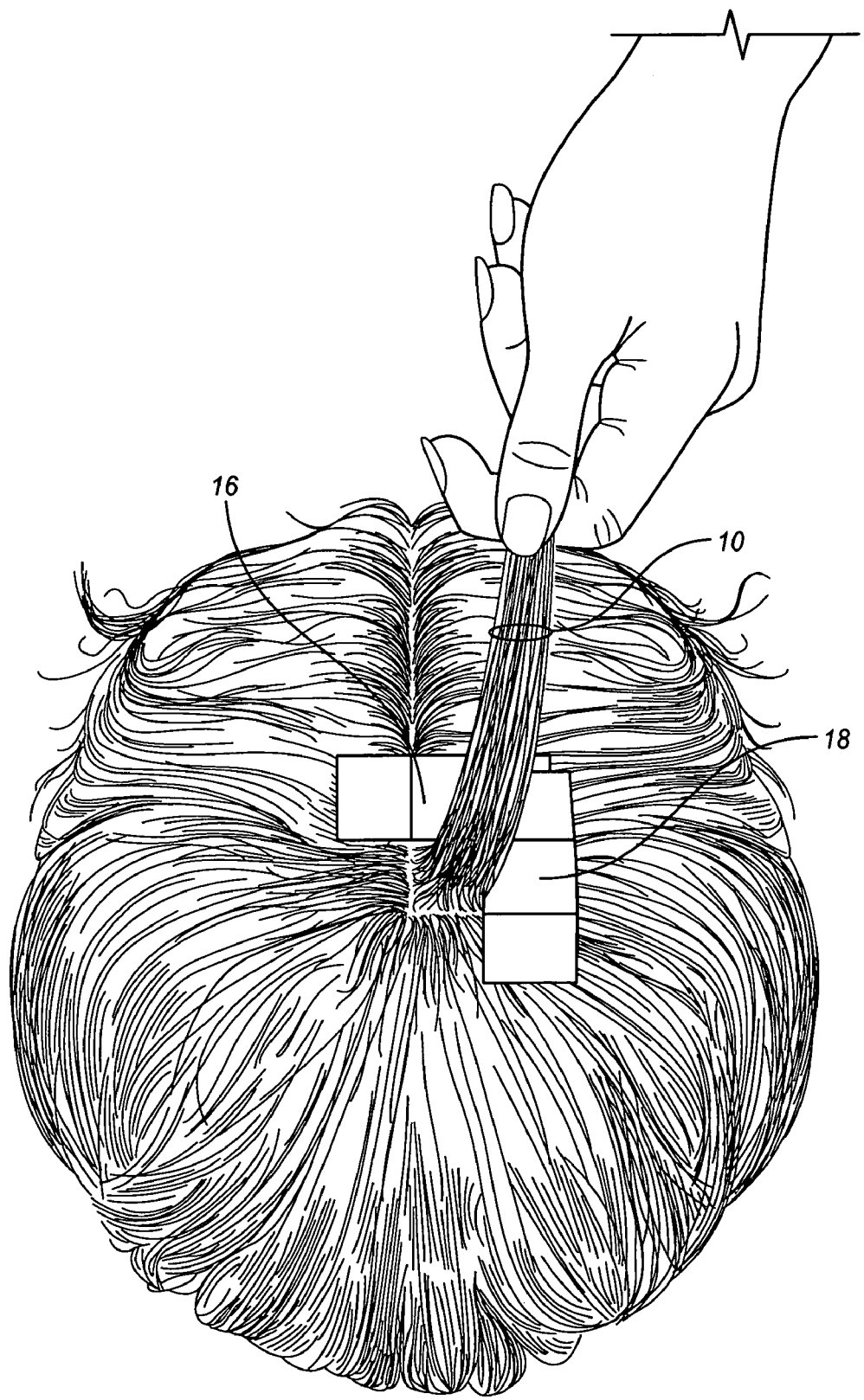
FIG. 2 is a top view of a scalp showing a section or bundle of hair that is combed from a delineated section of scalp and shows two sides of the section of scalp being delineated by gummed labels.
Figure 3:
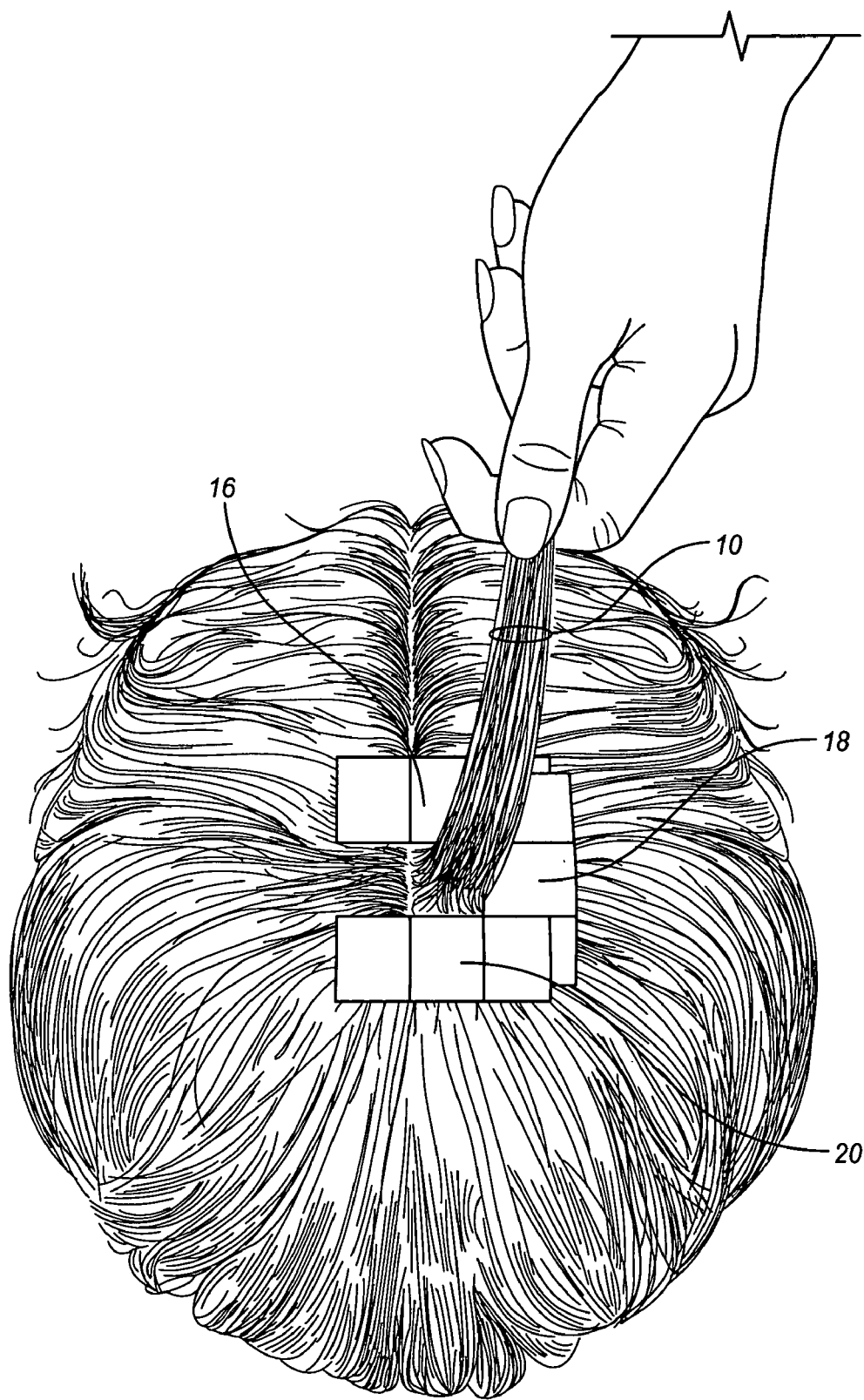
FIG. 3 is a top view of a scalp showing a section or bundle of hair that is combed from a delineated section of scalp and shows three sides of the section of scalp being delineated by gummed labels.
Figure 4:
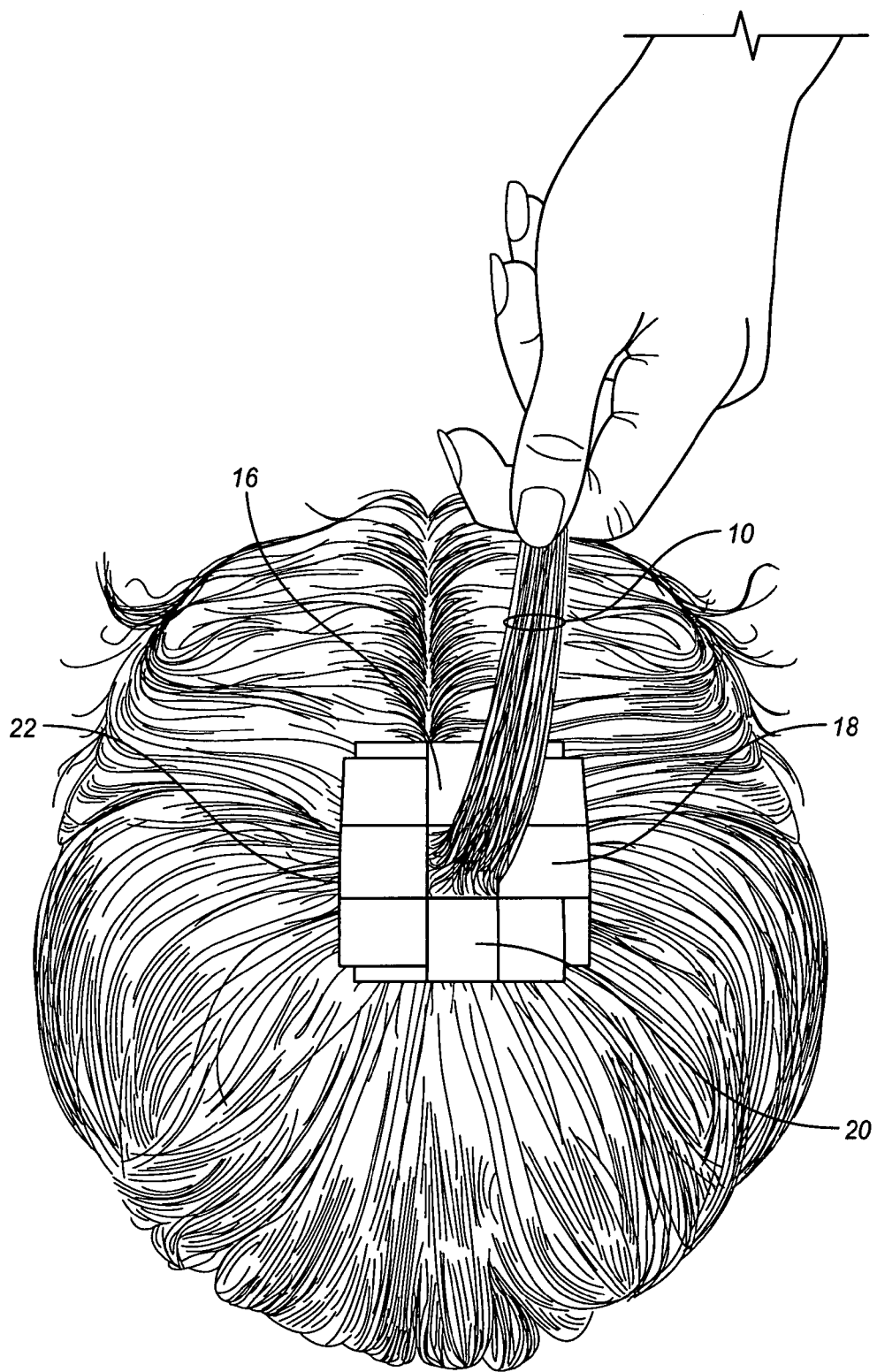
FIG. 4 is a top view of a scalp showing a section or bundle of hair that is combed from a delineated section of scalp and shows four sides of the section of scalp being delineated by gummed labels.

As shown in FIGS. 2–4, sequentially the delineated area of the scalp is fixed by gummed labels 18, 20 and 22. Each gummed label has a centimeter scale printed thereon so that the predetermined area, e.g., 2 square centimeters, can be measured and segregated by the gummed labels 16, 18, 20 and 22 from the rest of the hair on the scalp. The gummed labels 16, 18, 20 and 22 are printed with scale lines at intervals 2 cm apart. The color-coded lines are aligned with the edge of the preceding label and overlapped in a 4 step sequential fashion to create an isolated field of uncut hair that is 2 cm square.

Preferably, a 2×2 cm of scalp hair is manually isolated by combing the hair away from the designated square of hair-bearing scalp skin. This is done in a sequential fashion as described above. Care is taken to maintain a straight line at 90 degrees from the previous passage of the combing element 14.

Figure 5:
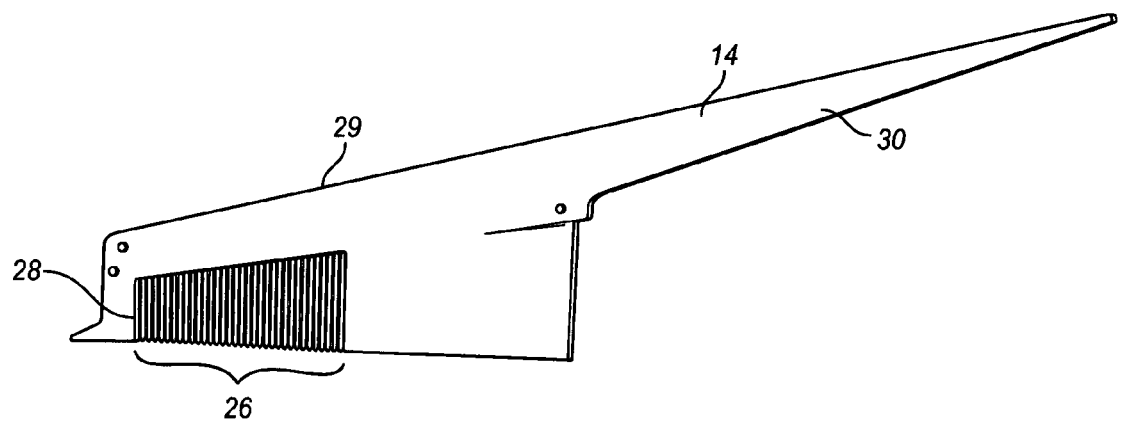
FIG. 5 is a plan view of one combing element.

The combing element 14 is shown in FIG. 5 and has a predetermined tine area 26, e.g., 2 cm long, with tines 28 and an upwardly sloping top edge 29 extending to a handle 30.

Figure 6:
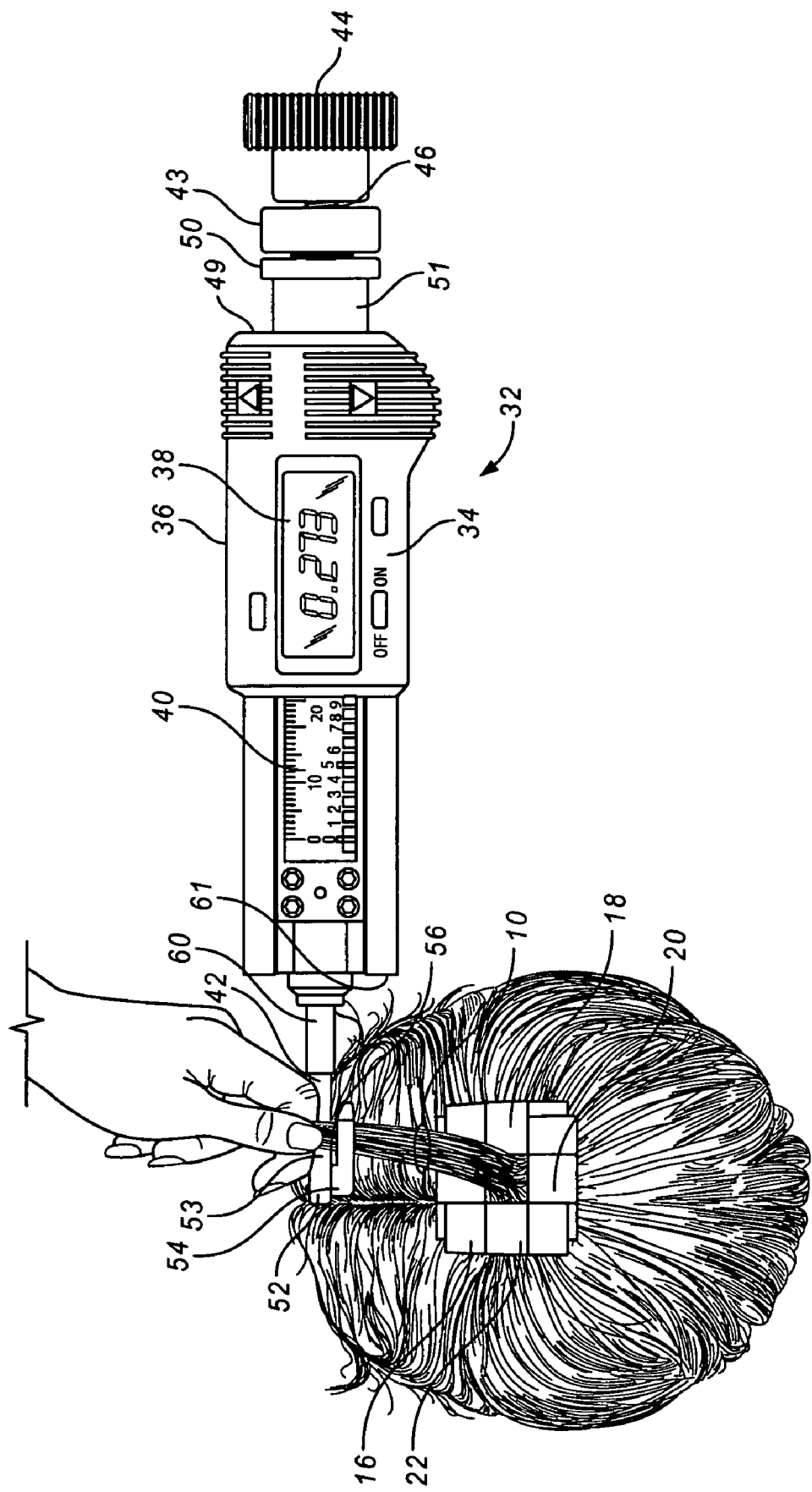
FIG. 6 is a top plan view of the scalp shown in FIG. 4 and a device constructed according to the teachings of the present invention for measuring the cross-sectional area of the bundle of hair.

A device 32 is provided, as shown in FIG. 6 for measuring the mass of hair in a bundle 10 from the 2 sq cm area of a hair bearing skin or scalp and compares that hair mass to the hair mass per sq. cm. in a permanent (normal) zone on the scalp.

The device 32 is an electronic caliper 34 having a body 36 with an electronic display 38 and a scale, gauge or analog display 40 for indicating the height or mass of hair in the hair bundle 10.

Figure 7:
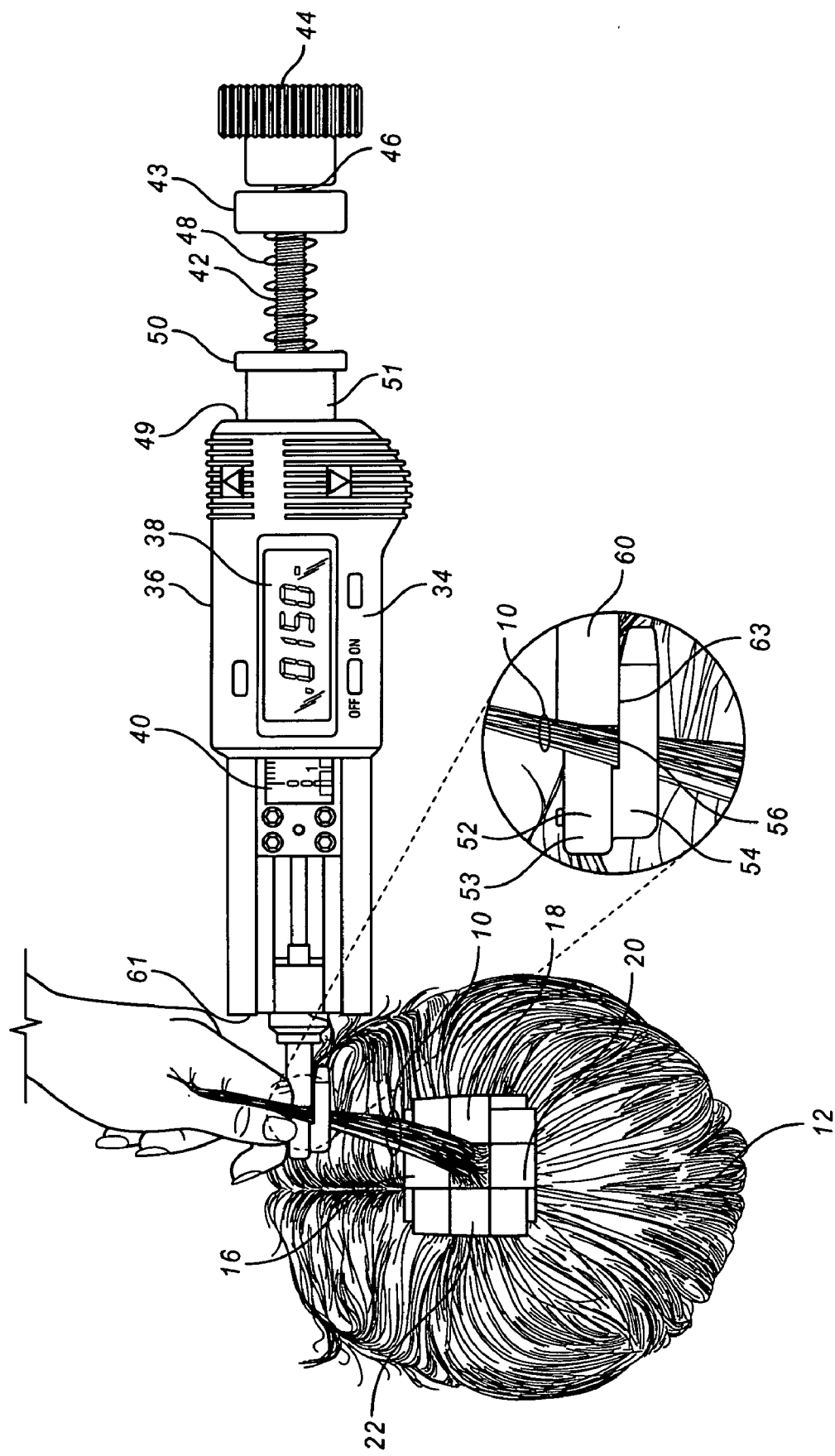
FIG. 7 is a top plan view of a scalp shown in FIG. 6 with a "J" shaped end of the device move toward a boss on the body of the device to measure the cross-sectional area of the bundle of hair positioned in a slot of the "J" shaped end.
Figure 8:
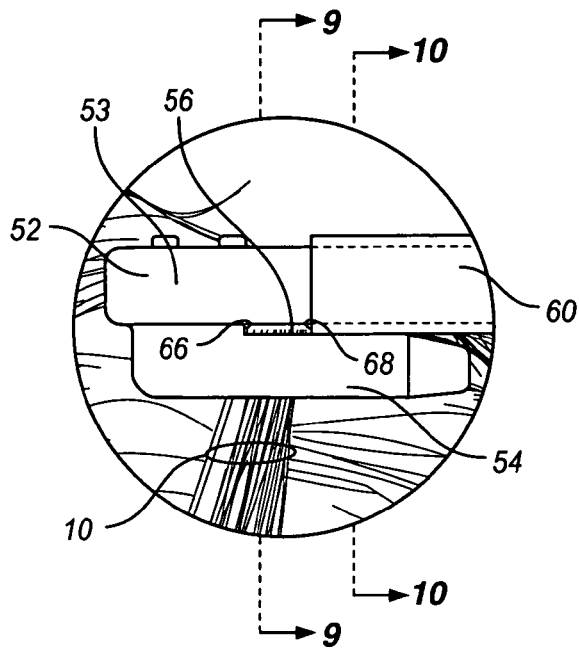
FIG. 8 is a fragmentary enlarged view of the hair trapped in the slot of the "J" shaped end.

The device 32 includes a piston or plunger 42 that extends through the body 36 and has a collar 43 thereon below a knob 44 at an outer end 46 of the plunger 42. A light weight return spring 48 (FIG. 7) bears against the collar 43 to urge the knob 44 away from an upper end 49 of the body 36 to push the plunger 42 upwardly. As shown a collar 50 between the spring 48 and the upper end 49 of the body of the body 36 is provided and has a reduced in diameter portion 51 that extends into the body 36.

It will be understood that the scale, gauge or analog display 40 moves with the plunger 42. Also, of course, the amount of movement of the plunger will be shown on the display 38.

The other end 52 of the plunger 42 has a "J" shape defined by a main leg 53 and a hook leg 54 with a slot 56 therebetween. The slot 56 can be 1 mm wide and 12 mm high.

Figure 9:
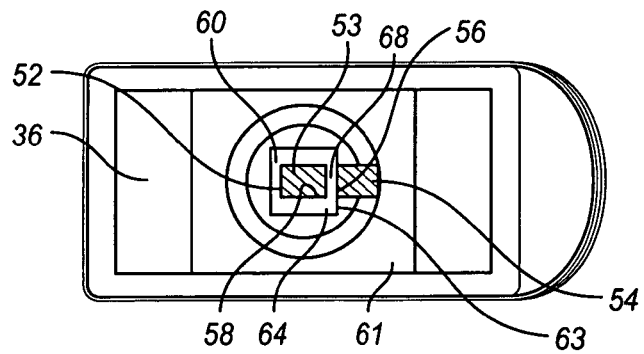
FIG. 9 is a cross-sectional view of the "J" shaped end taken along line 9—9 of FIG. 8.
Figure 10:
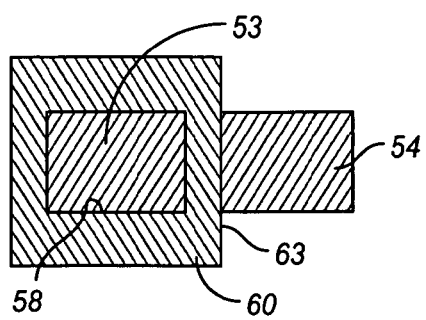
FIG. 10 is a cross-sectional view of a boss extending from the body of the device and in which the "J" shaped end is received.

The main leg 52 extends through a through bore 58 (FIG. 9) in a boss 60 at a lower end 61 of the body 36.

Figure 11:
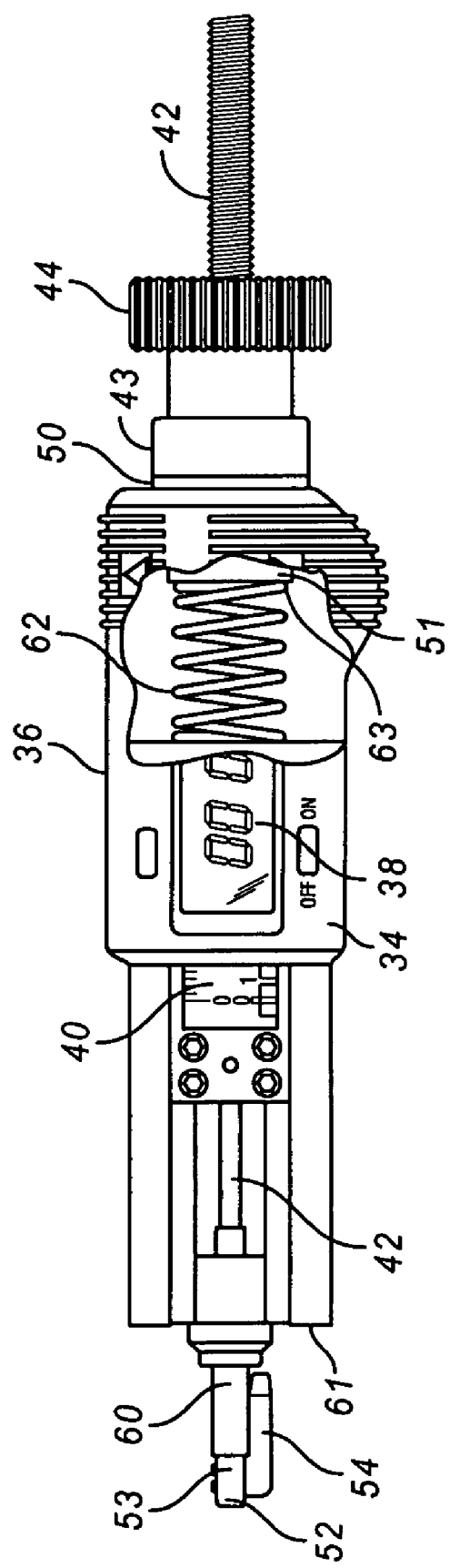
FIG. 11 is a plan view of the device without a bundle of hair in the slot of the "J" shaped end, shows the "J" shaped end moved over the boss, and is broken away to show a heavy compression spring In the body of the device.

As shown in FIG. 11 a heavy compression spring 62 in the body 36 bears against a lower end 63 of the reduced in diameter portion 51 of the collar 50.

A wall 64 of the boss 60 between the bore 58 and an outer surface 63 of the boss 60 is slidably received in the slot 56 upon relative movement between the boss 60 and the "J" shaped end 52.

The bundle of hair 10 is placed in the slot 56 and the knob 44 is screwed down on the plunger 42 and moves the reduced in diameter portion 51 of the collar 50 into the body 36 to compress the bundle of hair 10 between a bottom 66 of the slot 56 and an end surface 68 of the wall 54 (FIG. 9) with a predetermined compression established by the spring constant of the heavy spring 62 acting on the plunger 42. The end surface 68 defines an anvil 68 against which the bundle 10 of hair is compressed. In this way the device 32 defines a measuring device comprising the hair-holding slot 56, the "J" shaped end of the spring-loaded plunger 42 and the anvil 68.

The bundle or column 10 of hair is placed into the slot 66 and compressed against the anvil 68 in order to measure its height of the column or bundle 10 of hair. The anvil 68 and plunger are designed in a manner that always applies the same pressure to the column or bundle 10 of trapped hair. (This is accomplished with the heavy compression spring 62 bearing against the reduced in diameter portion of the collar 51) This is important because the hair bundle 10 is quite compressible. The mm height of the hair bundle or column 10 is read off a window on the electronic display 38 and/or off of the scale gauge or analog display 40. This arbitrary value shall be called the hair loss index or the density-diameter index. The procedure is performed in the balding area and the permanent area. The value for the balding area is divided by the value for the permanent area. The percent loss of hair mass in the balding is thus derived. When used to determine the efficacy of a hair growth product, before and after treatment evaluations are performed on the same area and compared.

Oddly, in pattern balding (Androgenetic alopecia), the back and sides of the scalp are immune to the thinning process which doctors call miniaturization. So that on a balding scalp, the permanent horseshoe shaped fringe is populated with normal sized hairs (70 microns) with a normal density—in the range of 150–250 hairs per square cm. On the top of the scalp, in the areas of hair loss, the population of hairs ranges in size from 70 microns to 15 microns in diameter with a wide range of hair diameters per square cm.

The cumulative number of hairs per sq cm of scalp times their cumulative diameters equals a value that might be best described as the hair mass. When the hair mass value of the balding zone is divided by the hair mass value of the normal permanent fringe (Zone 10), the percent loss of hair mass in the balding area is derived. When the hair mass value in an area of loss is compared with a subsequent measurement of the same area at a time in the future, the percent hair loss or growth may be derived.

This information is very important to those who care for patients with hair loss, and those who develop drugs or devices that promote hair growth. Again it must be emphasized that although the length of the hair does contribute to the total visual mass of hair, it is not considered because it varies with the cut length of the hair (styling) that has no relevance to intended application of this patent.

It will be understood that modifications can be made to the method and device of the present invention described above without departing from the teachings of the present invention.

For example, a mark can be placed on the body 36 and another mark placed on the plunger 42 and a separate caliper can be used to measure the distance between the marks for determining the height of hair compressed in the slot 56.

The heavy spring 62 can be omitted and the knob 44 can be tightened with a torque wrench to place a predetermined amount of compression on the bundle 10 of hair.

A simple protrusion with an anvil at the end can used in place of the boss 60 and received in the slot 56.

A simpler device can be provided including a body with the slot 56 therein and a piston having the anvil 68 at one end can be provided and positioned to be received in the slot 56. The body can be moved against the piston or the piston can be moved in and out of the slot 56.

The body and piston can be provided with a return spring, like spring 48, for holding the anvil 68 in the slot 56 until the spring is compressed to move the anvil 68 out of the slot 56.

If desired, side arms can be provided on the body, much like on a syringe, to facilitate gripping of the body while the piston or plunger is reciprocated or the knob 44 is rotated.

The non-isolated hair can be held down by other means, such as a ruler or hair clips instead of with gummed labels.

Further, the caliper can be mechanical or electrical/electronic, can be attached to the body or plunger or can be separate from the device 32.

Figure 12:
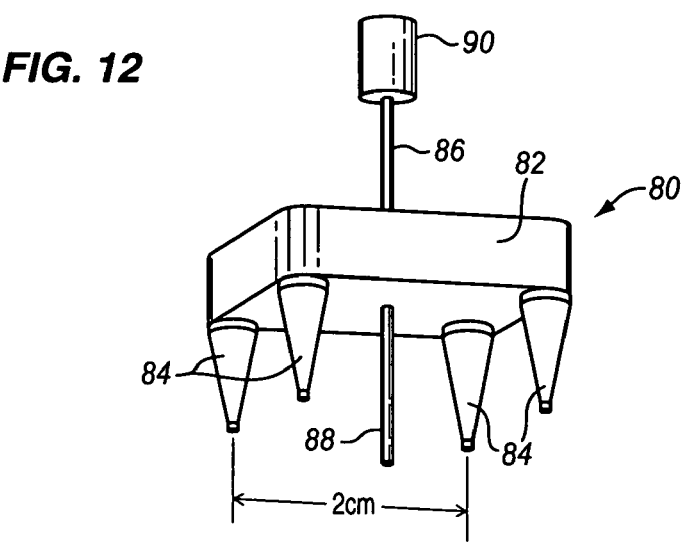
FIG. 12 is a perspective view of a marking template having a center locating pin and four ink marking pens, one at each corner of the template.

In FIG. 12 is illustrated a marking template 80 for marking the area on the scalp where a bundled hair is to be collected. The marking device 80 comprises a rectangular platform 82, preferably 2 cm square, having four depending ink pens 84 at the corners thereof. Then in the center of the platform 82 is a reciprocal pin 86 having a lower stylus 88 and an upper knob 90.

Figure 19:
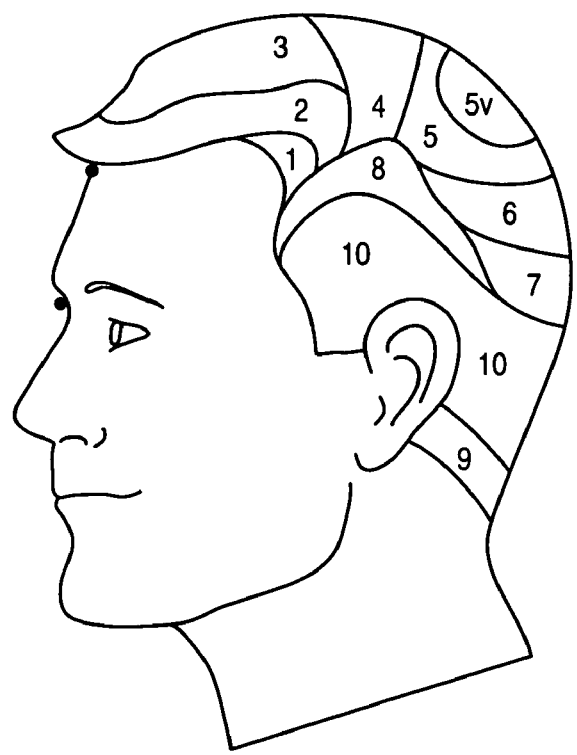
FIGS. 19 and 20 are side and top views of a head showing numbered hair zones on the scalp.
Figure 20:
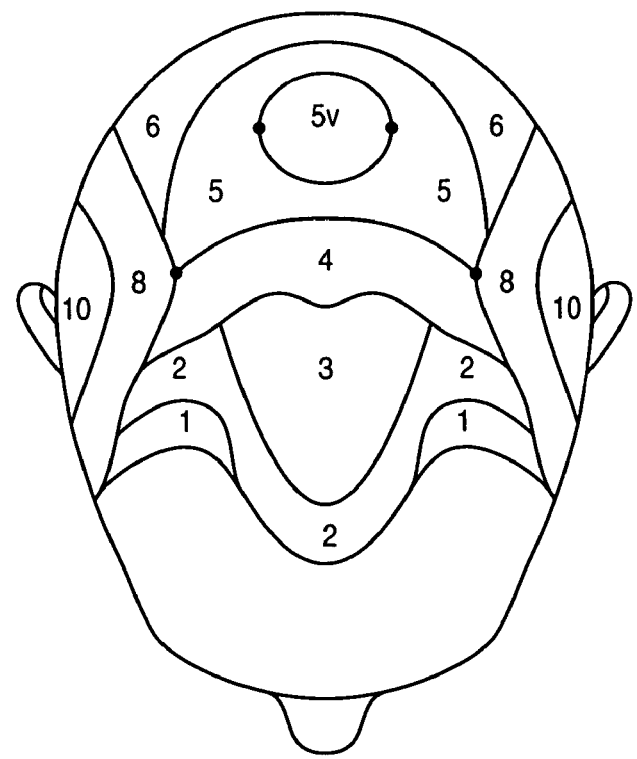

In the use of the marking device 80 a measurement is first made with a flexible measuring tape, not shown, from a place on the face to a zone on the scalp to a location on the scalp that is marked. See FIGS. 19 and 20. Typically the starting place for the measuring tape will be from the junction of the nose with the upper lip, namely, the base of the nasal columnella. The exact dimension to the scalp location mark is recorded so that repeat measurements can be made at substantially the same location mark. Permanent or semi-permanent skin tattoos may be used as an alternative.

Figure 13:
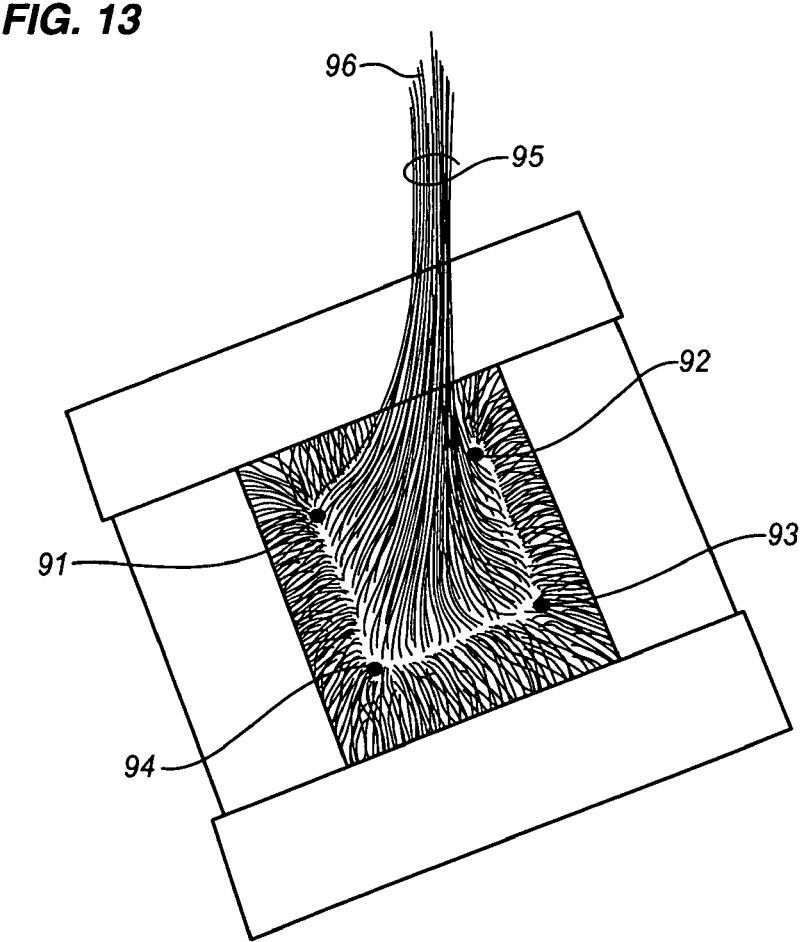
FIG. 13 is a marked off section of the scalp in one zone of the scalp where a hair measurement is being made.

The location marked in a zone of the scalp is then used by the marking template 80. In this respect, first the four pens 84 are dipped in ink. Then the stylus 88 of center pin 86 is positioned on the location mark just made on the scalp. Next, the marking template 80 is lowered so that the four ink pens 84 can make four ink marks 91–94 on the scalp as shown in FIG. 13. A bundle 95 of hair 96 is isolated and gathered up from the square area delineated by and within the four marks 91–94.

Figure 14:
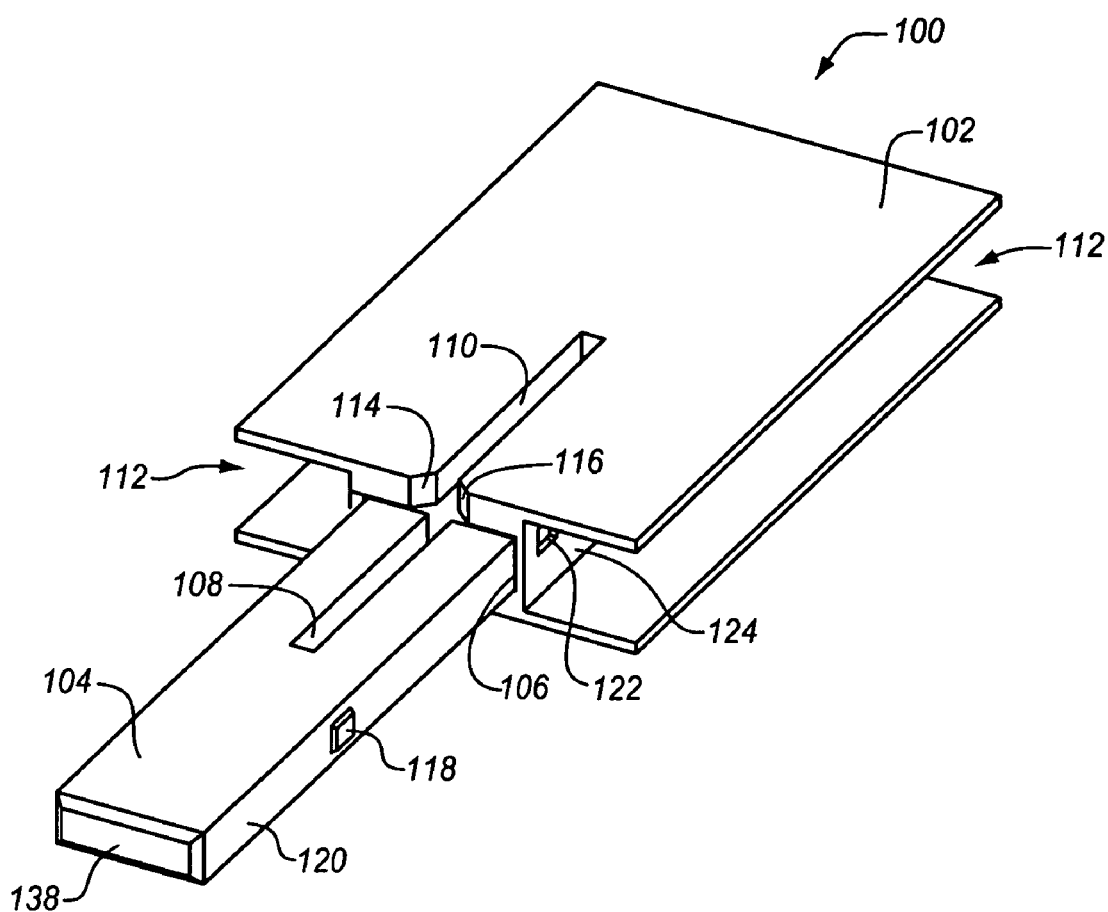
FIG. 14 is an exploded view of two parts of a cartridge with a length changeable slit therebetween for capturing the isolated hair shown in FIG. 13 for making a measurement of the bundle of hair isolated in FIG. 13.

In FIG. 14 is illustrated a two part cartridge 100 comprising a large rectangular part 102 and a smaller rectangular part 104 which is constructed for slidable rotation into a rectangular in cross section slot 106 in the larger part 102. The smaller rectangular part 104 has a transverse slit 108 therein that cooperates with a transverse slit 110 in the larger rectangular part 102. The transverse slit 110 also traverses the slot 106 in the larger rectangular part 102.

Preferably, and as shown in FIG. 14 the larger rectangular part 102 has a side slot 112 extending in and around three sides of the larger rectangular part 102 for receiving an "L" or "J" end of a plunger to be described hereinafter in conjunction with the description of FIGS. 15–18. The parts 102 and 104 can be made of any material and preferably are made of plastic.

The larger part 102 has, at the entrance to the transverse slit 110, diverging walls 114 and 116 at the side entrance to the transverse slit 110 to facilitate movement of the bundle 95 of hair 96 into the slit 110. The slits 108 and 110 and the cartridge parts 102 and 104 are constructed and arranged to capture the bundle 95 of hair 96 within the mating slits 108 and 110 when the smaller part 102 is moved into the slot 106 in the larger part 104.

While the dimensions of the slits 108 and 110 can vary the width of each slit 108 and 110 is preferably 1 mm and the length of each slit 108 and 110 is approximately 7–12 mm. The 1 mm width of the slits makes the height of compressed hair in the slits a simple number of value which is read off of a gauge and is not only the height of the bundle but also the cross sectional area of the bundle in square millimeters.

Preferably and as shown in FIG. 14 the smaller part has a recessed wing, tab, barb or detent 118 on at least one side wall 120 (or on opposite side walls) which is snap fittingly received in a hole 122 in a wall 124 between the slot 106 and the side slot 112 (or, for tow detents, in respective opposite holes in the walls of the slot 106). Of course, other cooperating structures can be employed, such as, for example, a spring-biased ball or detent and a mating hole. The detent 118 allows the smaller part 104 to be pushed into the slot 106 but only pulled part way out of the slot 106, that is to say, until the detent 118 snaps into the hole 122.

Either the smaller or larger part of the cartridge can be designed with an element extending approximately 10 mm outward from the mouth of the slit and parallel to walls of the slit. This structure is used to facilitate the gathering and directing of hair into the mouth of the slit and down into the slit.

Figure 15:
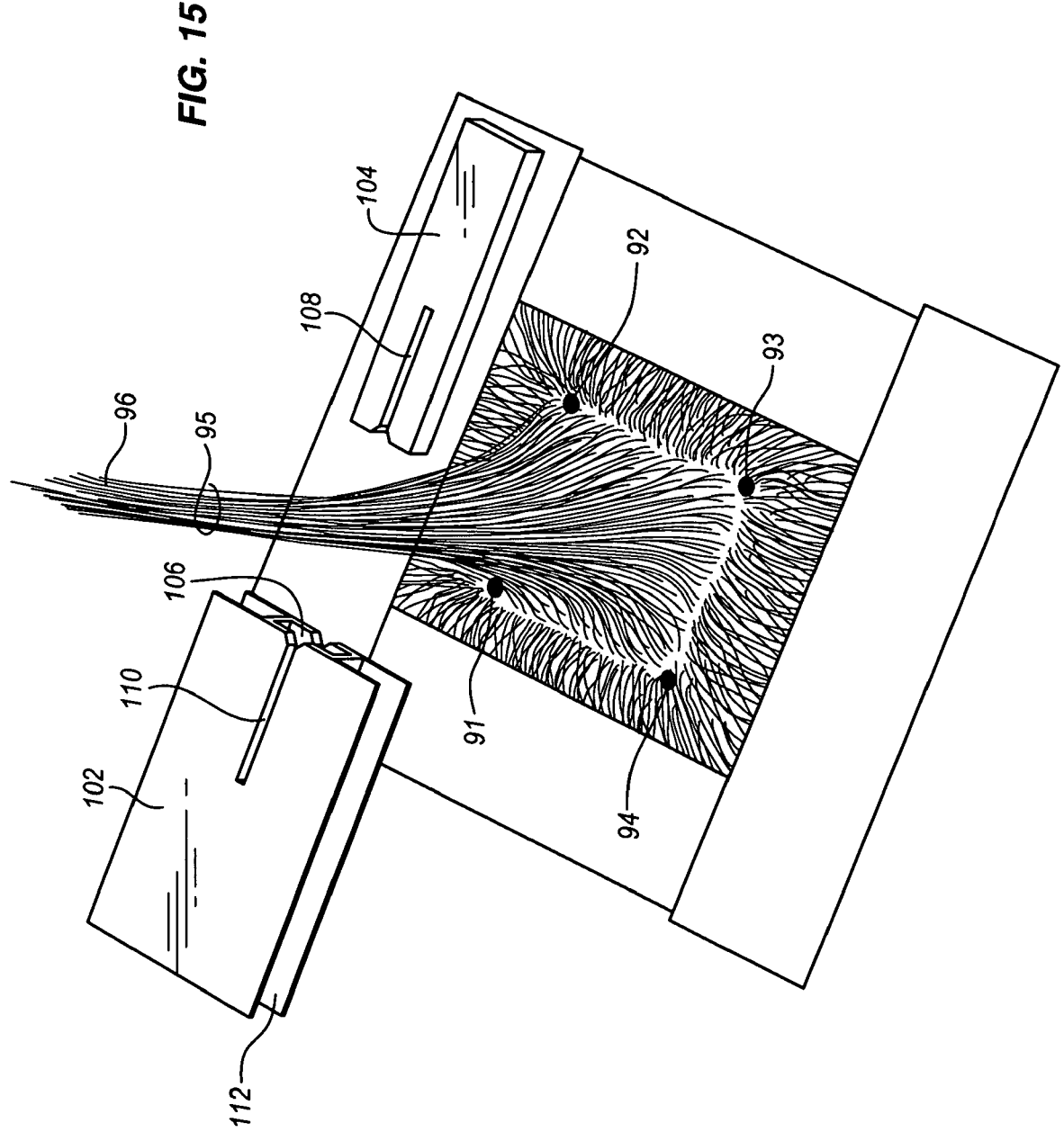
FIG. 15 is an exploded view of the cartridge showing the cartridge parts exploded ready to capture a bundle of hair isolated from the scalp.

As shown in FIG. 15, the two parts 102 and 104 are brought together about the bundle 95 of hair 96 isolated from the delineated scalp area with the smaller part 104 sliding into the slot 106 with the bundle 95 of hair 96 captured in the mating slits 108 and 110.

Figure 16:
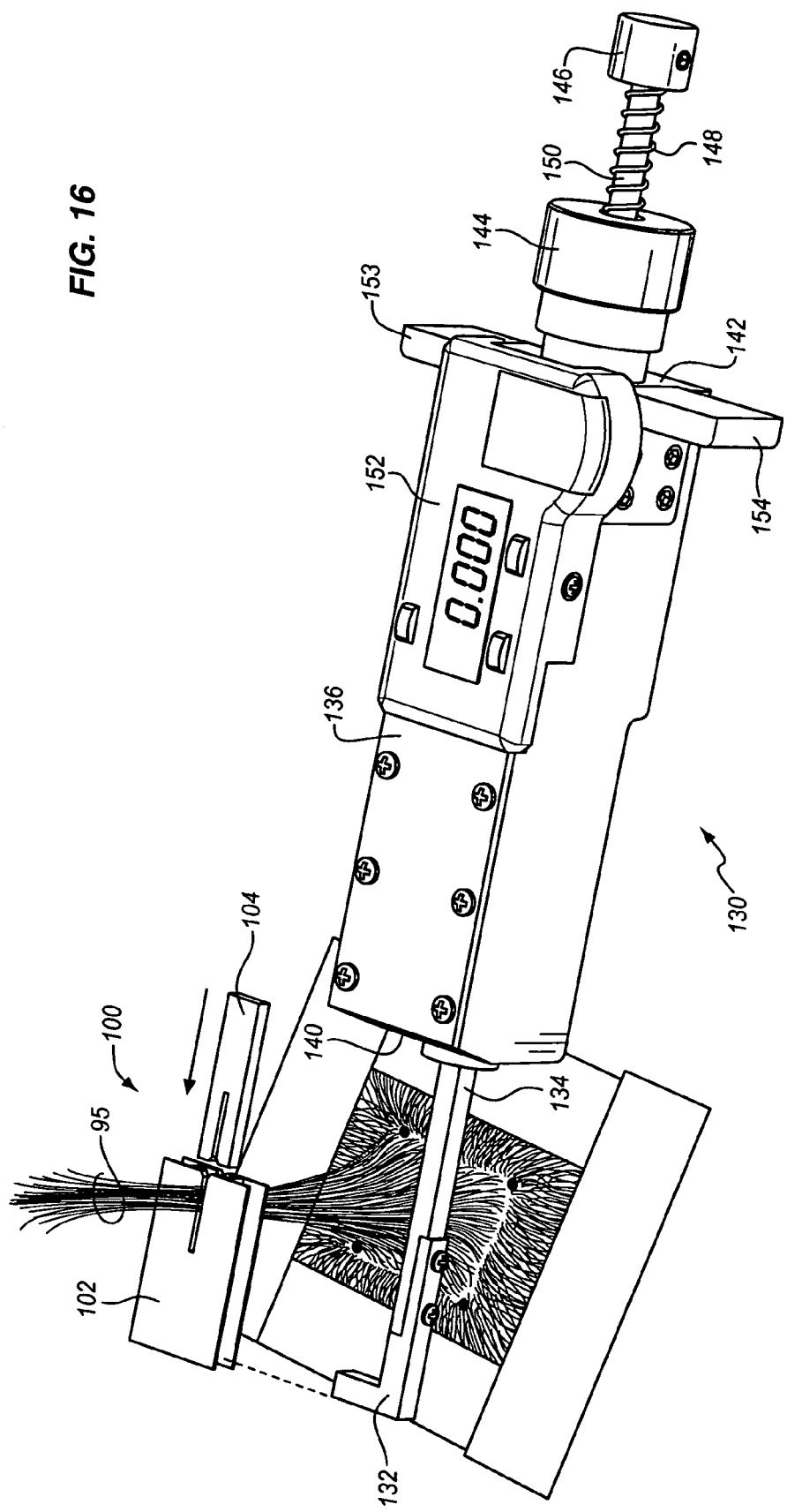
FIG. 16 is a perspective view of a measuring device having a plunger with an L shaped end which cooperates with the larger part of the cartridge for pushing the cartridge parts together between a first end of the device and an outer end of the L shaped plunger.

Then, as shown in FIG. 16, a measuring mechanism or device 130, similar to the device 32 is manipulated to move an L shaped end 132 of a plunger 134, that extends through a body 136 of the device 130, into engagement with the larger part 102 of the cartridge 100, namely into the side slot 112 in the larger part 102. The slot 112 in peripheral three sides of the larger part 102 ensures that there is no cross contamination between oil or other material on the bundle 95 of hair 96 from one measurement to the bundle of hair of another measurement, since the cartridge 100 can be discarded and the cartridge 100 is fully isolated from the device 130 and particularly the L shaped end 132.

An outer end 138 (FIG. 14) of the smaller part 104 is positioned adjacent a first or inner end 140 of the body 135 of the device 130 for being urged against the outer end 138 by the L shaped end 132 when a knob (146) is released, to compress the bundle 95 of hair 96 in the slits 108 and 110.

Figure 17:
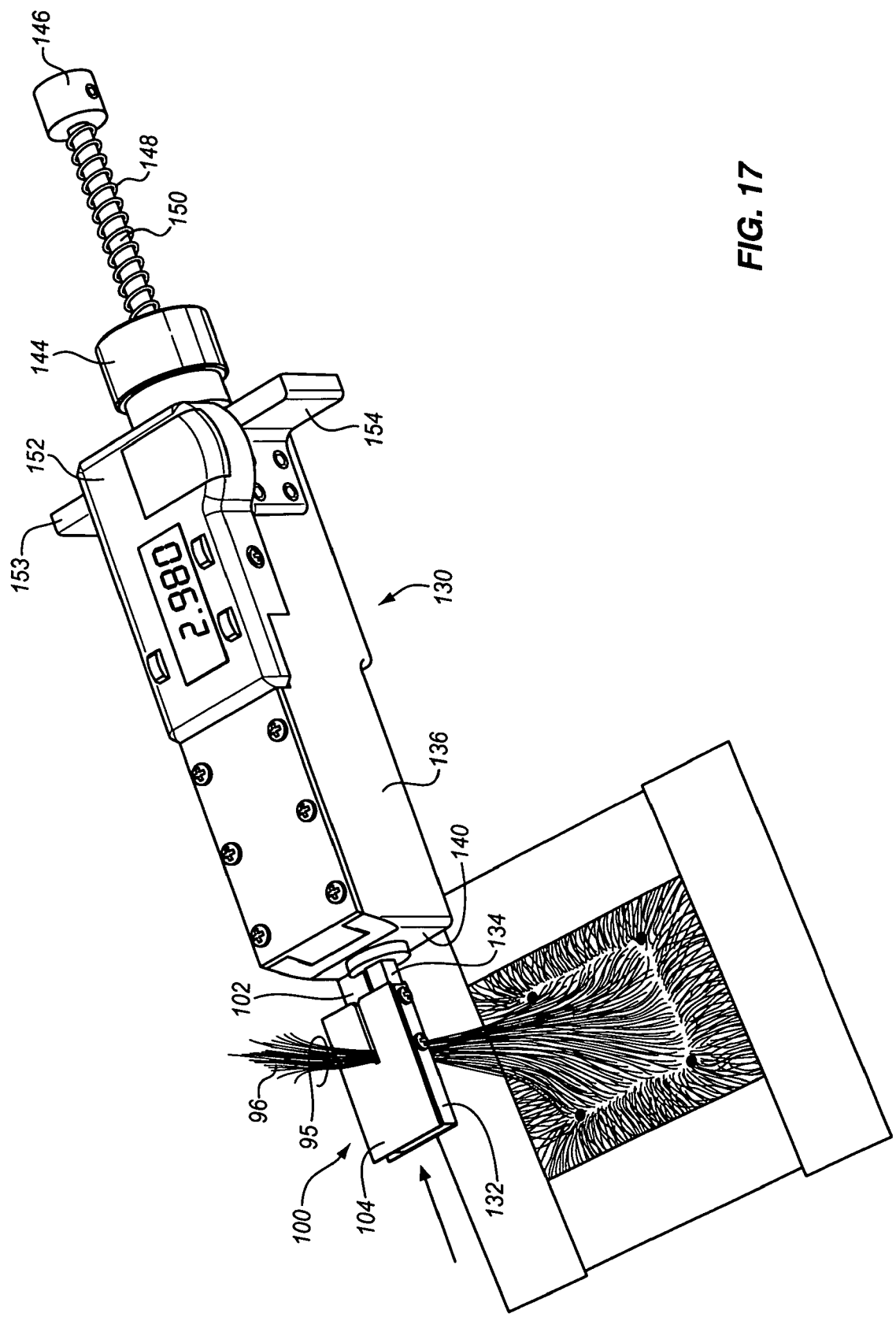
FIG. 17 is a perspective view of the parts of the cartridge pushed together by the L shaped plunger which is forced toward the first end of the device by the action of a spring on the other end of the plunger at the other end of the device shows the measurement of the compressed bundled hair in the engageable length slit and shows how the cartridge sheathes the L shaped plunger to protect it from contact with the surrounding hair.

The plunger 134 extends out of a second or outer end 142 of the body 136, where a collar 144 is located, to a knob 146. A spring 148 is positioned on an outer portion 150 of the plunger 134 that extends to the knob 146 and between an internal shoulder (not shown) within the collar 144 and the knob 146. It will be understood that the knob 146 is pushed toward the body 136, compressing the spring 148, to extend the L shaped end 132. Then, after the cartridge 100 is positioned on the L shaped end 132 with the bundle 95 of hair 96 trapped therein, the knob 146 is released so that the two parts 102 and 104 of the cartridge are pushed toward each other to compress the bundle 95 of hair 96 in the mating, changeable length slits 108 and 110, as best shown in FIG. 17. The length of the mating slits 108 and 110 when a bundle of hair is compressed therein typically ranges from 1 to 4 mm with a constant width of 1 mm. This measurement is shown on an electronic gauge 152 fixed on the body 136 of the device 130. The spring 148, and perhaps another spring in the body 136, provide a constant compression force, for all compression measurements on a bundle of hair captured in the mating, changeable length, slits 108 and 110. Tests have shown that the measurements are very accurate and a difference of four hairs in a bundle resulted in measurements of 3.34 and 3.35. This measurement is referred to as the DDI or Density-Diameter Index and represents the cumulative density and diameter of all hairs in the bundle 95. In the illustrated test, a DDI of 2.98 is shown.

The device 130 preferably, also has two sides of arms or handles 153 and 154 adjacent the outer end 142 of the body 136, much like a syringe, to allow the device 130 to be grasped like a syringe for moving the L shaped end 132 of the plunger 134 inwardly and outwardly.

Figure 18:
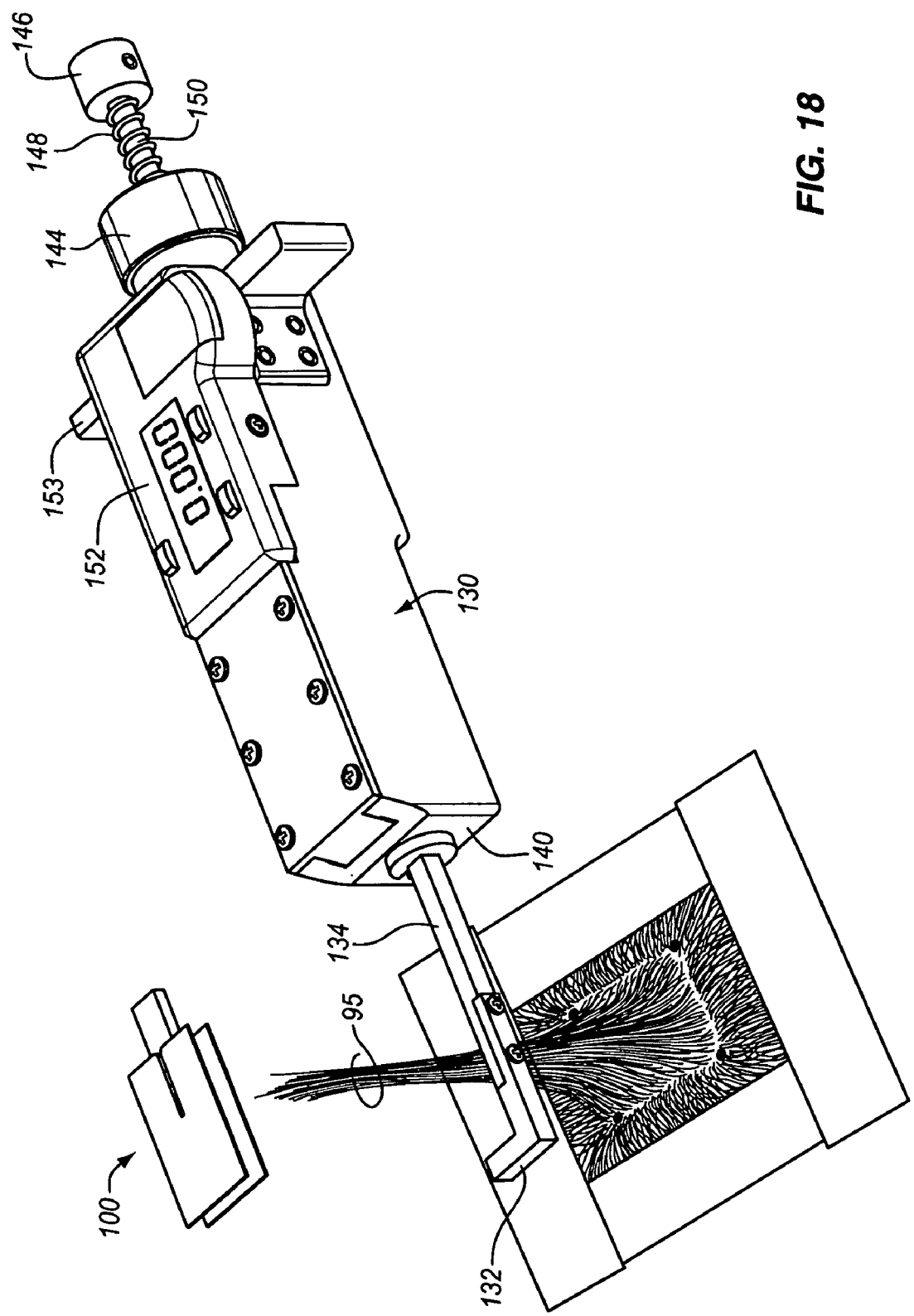
FIG. 18 is a perspective view of the device with the plunger moved outwardly again and the cartridge removed from the bundle of hair with the smaller part of the cartridge moved out a short distance from the larger part to allow the bundle of hair easily to be pulled out of the slit in and between the cartridge parts.

After the measurement is made, the inner smaller part 104 of the cartridge 100 is pulled slightly out from larger part 104 until the detent 118 engages the hole 122 to slightly increase the length of the mating slits 108 and 110 thereby to allow the cartridge easily to be moved off of the bundle of hair as shown in FIG. 18. Then the cartridge 100 can be disposed of so that each cartridge 100 only has a single use. This ensures that there is no cross contamination between oil or other material on the hair from one measurement to the hair of another measurement.

The cartridge 100 and the device 130 provides a simple and efficient structure for measuring bundled hair and facilitate the method of measuring the DDI of a bundle of hair and enable accurate repeat measurements to be made of a bundle of hair in a particular selected zone on the scalp. Of course hair in other zones 1–10, (FIGS. 19 and 20) also can be measured.

The device 32 and the device 130 and cartridge 100 have a number of advantages some of which have been described above and others which are inherent in the device 32 or 130, the cartridge 100 and the methods of using same for measuring DDI.

Accordingly, the scope of the invention is only to be limited as necessitated by the accompanying claims.

What is claimed is:

1. A method of isolating a predetermined area of hair-bearing skin and measuring the combined cross section of uncut hair within the area comprising the steps of:
   defining a pre-measured hair site on a scalp;
   isolating a bundle or column of uncut hair from the site;
   providing a measuring device with a hair-receiving slot;
   placing the bundle or column of hair in the hair receiving slot;
   moving a bottom of the slot with a mechanical assembly and without hand compression against an anvil received in the slot to place a predetermined precise amount of compression force on variable-sized bundles of uncut hair placed in the slot;
   measuring the height of the compressed bundle or column of uncut hair in the slot; and, comparing the height of hair measured with the height of other hair measurements of a similar bundle of hair from the same or a different site location on the scalp.

2. The method of claim 1 wherein the pre-measured site on the scalp is approximately 2 cm by 2 cm square.

3. The method of claim 2 including the step of defining the 2 cm×2 cm area with a stenciling template and a marking pen.

4. The method of claim 2 including the step of defining the 2 cm×2 cm area with an inked footed template.

5. The method of claim 1 wherein the slot is 1 mm wide by approximately 7 mm to 12 mm high.

6. The method of claim 1 wherein said step of locating is accomplished by measuring a predetermined distance from a predetermined point on a face to the site location on the scalp.

7. The method of claim 6 including the step of using a calibrated tape to measure the predetermined distance from the predetermined point on the face to the site location on the scalp.

8. The device of claim 1 where the area of scalp having the hair to be measured has an areal extent of from 2 square centimeters up to 4 square centimeters.

9. A two-part cartridge for use in measuring a bundle of hair isolated from the scalp, said cartridge comprising a first, larger, generally rectangular part having a top and a bottom and four sides with a slot having a generally rectangular cross section extending into the first part from one side thereof, said first part having a transverse first slit traversing the slot and extending though the top and bottom of the first part and extending inwardly from the one side of the first part, a second, smaller, rectangular part having a generally rectangular cross section with the same shape and size as the cross section of the slot in the first part and adapted to be received in said slot, said second part having an inner end and an outer end with a second slit extending transversely through the second part from the inner end, said second slit having approximately the same width as the first slit and is adapted to mate with the first slit in the first part when the second part is inserted into the slot in the first part.

10. The cartridge of claim 9 wherein said slits have a width of 1 mm.

11. The cartridge of claim 10 wherein said slits have a length between approximately 7 mm and 12 mm.

12. The cartridge of claim 9 wherein an elongated side of said smaller second part and a wall of said slot in said first part have cooperating detent and recess structure which engage when the second part is pulled part way out of the first part.

13. The cartridge of claim 9 wherein said first part has a side slot in the other three sides of said first part which is constructed and arranged to receive an L shaped arm of a measuring device for sheathing and protecting the L shaped arm.

14. A device for measuring a bundle of hair isolated from a predetermined location on a scalp, said device comprising a body, said body having a first end and a second end, a plunger extending through said body, said plunger having an L shaped end extending from said first end of said body and a plunger outer portion extending from said second end and having a knob at the outer end thereof, a spring between said knob and said body on said outer portion of said plunger, a gauge on said body for measuring the movement of said L shaped arm toward said first end of said body, structure having a changeable length slit therein adapted to be mounted on said L shaped arm when said L shaped arm is extended, said structure being manipulated to gather a bundle of hair in said changeable length slit, said knob then being pushed to extend said L shaped arm to mount said structure thereon followed by said knob being released so that said spring acting between the second end of the body and said knob cause said L shaped arm to push said structure towards said first end of said body to cause the bundle of hair to be compressed in said changeable length slit and the height of the bundle of hair in said changeable length slit being measured by said gauge on said body.

15. The device of claim 14 wherein said structure comprises a two-part cartridge comprising a larger generally rectangular first part having a slot in a side thereof and a smaller generally rectangular second part which is received in said slot, said first part having a first slit extending therethrough traversing said slot and said second part having a second slit extending therethrough and adapted to mate with said first slit in said first part when said second part is inserted into said slot, said first and second slits forming and defining said changeable length slit, said first part being mounted on the L shaped arm after said L shaped arm is extended from said body by pushing on said knob against the spring, said first part and said second part being positioned about a bundle of hair which is moved into said first and second slits when said second part is moved into said first part to capture the bundle of hair in said first and second slits.

16. A device for measuring the cross-sectional area of a bundle of uncut hair from a pre-measured area of hair-bearing skin, said device comprising a body, a plunger extending through said body and out one end of said body, a wall surface defining an anvil at said one end of said body, a compressing mechanism associated with said body for applying a predetermined amount of pressure on said plunger, said plunger extending through said wall surface and having a "J" shaped end defined by a main leg portion extending through said wall surface and a hook leg portion, said two leg portions defining a hair receiving slot therebetween, and hair received in said slot being compressed between a bottom of said slot and said anvil, and measuring means associated with said body and associated with said plunger for measuring the extent of movement of said plunger when compressing the bundle of hair.

17. The device of claim 16 wherein said measuring means include one of an integrated or separate measuring caliper with a visual display for indicating the height of compressed uncut hair in said slot when said "J" shaped end of said plunger is moved toward said anvil with a bundle of uncut hair in said slot.

18. A two part cartridge for use in measuring or indicating the cross sectional area of a bundle of uncut hair isolated from a location on a scalp, said cartridge comprising an anvil portion in one part of the cartridge against which a bottom of a slot in the other part of the cartridge is compressed by a separate mechanism.

19. The cartridge of claim 18 combined with a mechanism for compressing a bundle of uncut hair received in said slot between said anvil portion and said bottom of said slot.

20. The cartridge of claim 18 combined with a device for measuring or indicating the amount of movement between said bottom of said slot and said anvil when a bundle of uncut hair is received in said slot and compressed in said slot.

21. The cartridge of claim 18 combined with an integrated or separate measuring caliper having a visual display for use with said cartridge for indicating the height of compressed uncut hair in said slot when said slot bottom and said anvil.

22. A device for use in measuring the cross-sectional area of uncut hair from a pre-measured area of hair-bearing skin, said device comprising:
   a J shaped plunger having a slot with a bottom for receiving a bundle of hair,
   a body having an anvil positioned adjacent said slot,
   a compressing mechanism associated with one of said plunger or anvil for placing a predetermined precise amount of compressive force on different sizes of bundles of hair placed in said slot, and
   a mechanism for causing relative movement between said bottom of said slot and said anvil to compress the bundle of hair by the predetermined, precise amount of compressive force.

23. The device of claim 22 including a device for measuring or indicating the amount of movement between said bottom of said slot and said anvil when a bundle of hair is received in said slot and compressed in said slot.

24. The device of claim 23 wherein said measuring or indicating device includes a scale, gauge or analog display for measuring or indicating the height of compressed hair in said slot when said "J" shaped end of said plunger is moved toward said anvil with a bundle of uncut hair in said slot.

25. A device for use in measuring the cross-sectional area of a bundle of uncut hair from a pre-measured area of hair-bearing skin, said device having a slot for receiving a bundle of uncut hair, an anvil positioned adjacent said slot for being received in said slot upon relative movement between said anvil and said slot, and a mechanical assembly associated with one of said slot or said anvil for compressing the bundle of uncut hair with a predetermined, precise amount of compressive force between said anvil and a bottom of said slot, said mechanical assembly being mechanically limited to place no more or less than the predetermined, precise amount of compressive force on variable-sized bundles of uncut hair placed in said slot.

26. The device of claim 25 including a mechanism for measuring or indicating the height of the compressed hair in said slot including one of an integrated or separate measuring caliper with a visual display for indicating the height of compressed uncut hair in said slot when relative movement is established between said anvil and said bottom of said slot with a bundle of uncut hair in said slot.

27. A device for use in measuring the cross-sectional area of uncut hair from a pre-measured area of hair-bearing skin, said device comprising a body having a slot for receiving a bundle of hair, an anvil positioned adjacent said slot, a compressing mechanism associated with one of said body or anvil for placing a predetermined precise amount of compressive force on different sizes of bundles of hair placed in said slot, and a mechanism for causing relative movement between said body having said slot and said anvil to compress the bundle of hair by the predetermined, precise amount of compressive force.

28. The device of claim 27 including a device for measuring or indicating the amount of movement between said body and said anvil when a bundle of hair is received in said slot and compressed in said slot.

29. A device for use in measuring the cross-sectional area of uncut hair from a pre-measured area of hair-bearing skin, said device having a slot for receiving a bundle of hair, an anvil positioned adjacent said slot, a compressible element associated with one of said slot or anvil for placing a predetermined precise amount of compressive force on different sizes of bundles of hair placed in said slot, and a mechanism for causing relative movement between said slot and said anvil to compress the bundle of hair by the predetermined, precise amount of compressive force.

30. The device of claim 29 including a device for measuring or indicating the amount of movement between said slot and said anvil when a bundle of hair is received in said slot and compressed in said slot.

* * * * *